United States Patent
Tiwari et al.

(10) Patent No.: US 7,481,908 B2
(45) Date of Patent: Jan. 27, 2009

(54) SYSTEM AND A PROCESS FOR OBTAINING HIGH PURITY PHENANTHRENE FROM PHENANTHRENE ENRICHED COAL TAR FRACTION

(75) Inventors: Kaushal Kishore Tiwari, Jharkhard (IN); Sukuru Ramakrishna Rao, Jharkhard (IN); Sanjay Kumar Thakur, Jharkhard (IN); Somnath Banerji, Jharkhard (IN)

(73) Assignee: Council of Scientific & Industrial Research, New Delhi (IN)

( * ) Notice: Subject to any disclaimer, the term of this patent is extended or adjusted under 35 U.S.C. 154(b) by 292 days.

(21) Appl. No.: 10/107,284

(22) Filed: Mar. 26, 2002

(65) Prior Publication Data

US 2003/0183499 A1 Oct. 2, 2003

(51) Int. Cl.
*B01D 3/14* (2006.01)
*B09B 3/00* (2006.01)
*C10C 1/04* (2006.01)

(52) U.S. Cl. .............. 203/74; 201/3; 201/21; 201/24; 201/30; 203/80; 203/87; 208/42

(58) Field of Classification Search .......... 201/3, 201/21, 24, 30, 45; 203/47, 74, 80, 87; 208/41, 208/42
See application file for complete search history.

(56) References Cited

U.S. PATENT DOCUMENTS

| 2,590,096 | A | * | 3/1952 | Feldman et al. | 203/63 |
| 2,675,345 | A | * | 4/1954 | Andrews | 203/48 |
| 3,624,174 | A | * | 11/1971 | Sugerman | 203/48 |
| 3,850,757 | A | * | 11/1974 | Looney | 203/9 |

* cited by examiner

Primary Examiner—Virginia Manoharan
(74) Attorney, Agent, or Firm—Abelman, Frayne & Schwab

(57) ABSTRACT

The present invention relates to a system and a process for obtaining phenanthrene of about 95% purity from coal tar distilled fraction containing crude phenanthrene by performing fractional distillation at a reduced pressure of 50 mm mercury and at a temperature range of 160-180° C. to obtain first distilled fraction containing acenaphthene and fluorene; a second distillate fraction at a temperature range of 200-230° C. containing phenanthrene, anthracene and traces of carbazole; followed by re-distilling the second distillate fraction at a temperature range of 210-224° C. to finally obtain pure phenanthrene and a residue which is again used for the recovery of residual phenanthrene by re-distillation at a temperature range of 210-224° C.

2 Claims, 1 Drawing Sheet

Figure 1:
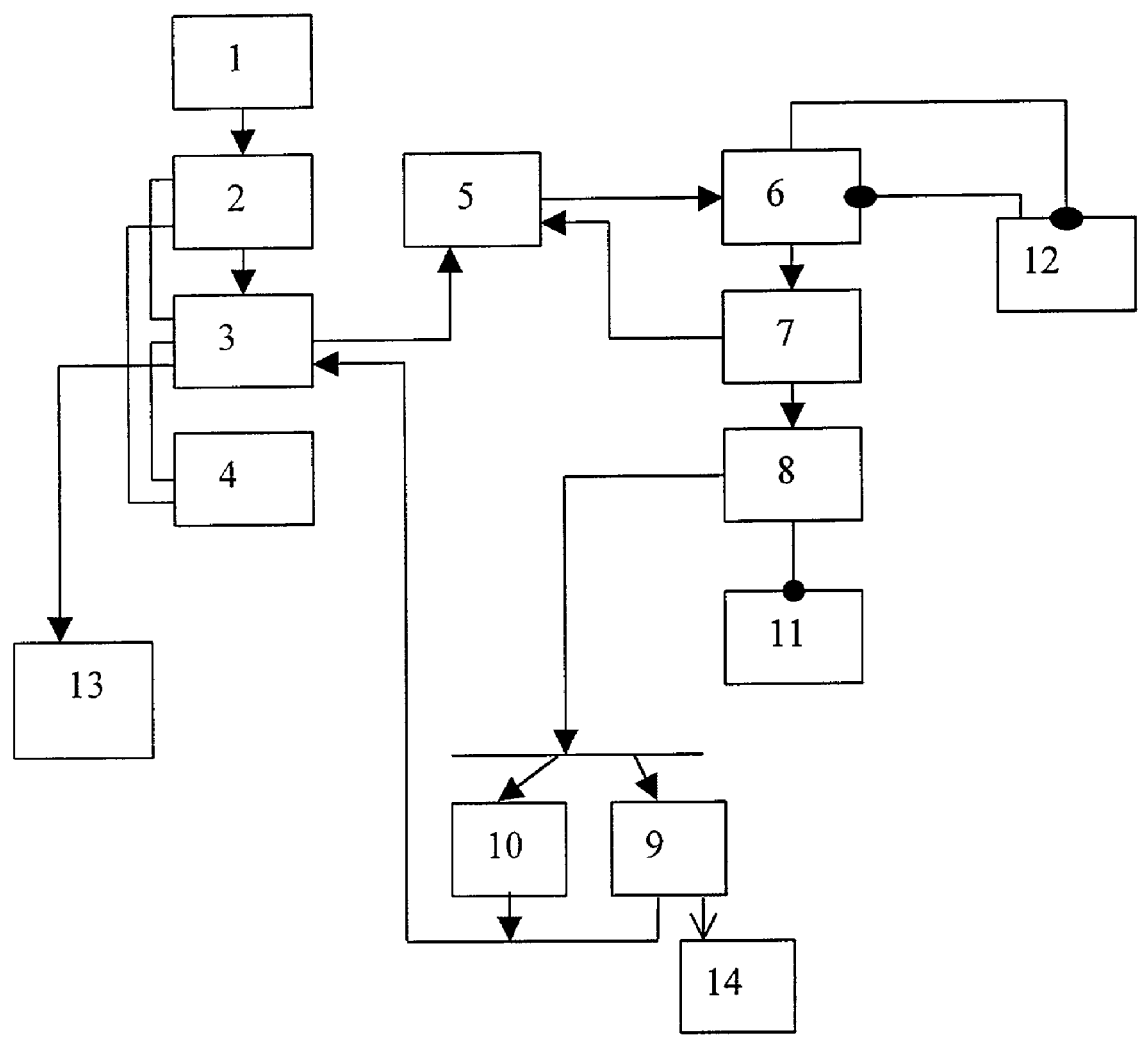

SYSTEM AND A PROCESS FOR OBTAINING HIGH PURITY PHENANTHRENE FROM PHENANTHRENE ENRICHED COAL TAR FRACTION

FIELD OF THE INVENTION

The present invention relates to a process to obtain about 95% purity Phenanthrene and a system for obtaining the said product from coal tar distilled fraction containing crude phenanthrene.

BACKGROUND AND PRIOR ART REFERENCE

Phenanthrene forms the basis for production of 9,10-phenanthraquinone and 2,2'-diphenic acid. It can also be used to synthesize anthracene via the isomerisation product of sym-octahydrophenanthrene. Electrically conductive substances, e.g., for use in batteries and solar cells, can be produced by the electrochemical conversion of phenanthrene diazonium salts in a solvent containing a conductive salt and subsequent doping with various ions (like sodium, barium, hydrogen etc). Liquid crystalline 7-n-alkyl-9, 10-dihydrophenanthrene-2-carboxylic acid ester, used for optical-electronic applications, can be synthesized from 9,10-dihydrophenanthrene. By cross-linking with p-xylene glycol and 4-toluenesulphonic acid, poly-condensed thermosetting resins are obtained for composites or temperature-resistant, electrically insulating coatings. A polyamide-polimide resin can be produced by oxidation of phenanthrene to phenanthrene-9,10-quinone and 9,10-diol, condensation with formaldehyde, oxidation to the polycarboxylic acid, formation of the anhydride and finally reaction with an aromatic diamine. This resin is suitable for use in high temperature insulators, printed circuit boards, and laminates. Phenanthrene has been proposed as a plasticizer for plastics and molding compounds; phenanthrene and alkylphenantherenes have been suggested as stabilizers for mineral oil products.

Phenanthrene, at a concentration of 5%, is the second most important coal tar constituent in terms of quantity after naphthalene. During primary distillation of coal tar, it is concentrated in the anthracene oil fraction. After crystallization of the anthracene residues, the phenanthrene is recovered as a fraction from the filtrate of this crystallization, or from the top fraction of crude anthracene distillation, by re-distillation. Technically pure grades of phenanthrene are obtained by sulfuric acid refining and re-crystallization from methanol, or by repeated rectification of the phenanthrene fraction. The accompanying substances can be separated either by partial sulphonation, or by partial condensation with formaldehyde and hydrogen chloride. Detailed search on patent databases and other literature did not result in any relevant reference.

OBJECTS OF THE INVENTION

The main object of the invention is to provide a process for obtaining high purity phenanthrene from crude phenanthrene, which obviates the drawbacks as detailed above.

Another object of the invention is to extract acenaphthene, carbazole and fluorene contained in the crude phenanthrene fraction.

Still another object of the invention is to provide a system for the enhancement of purity of phenanthrene.

SUMMARY OF THE INVENTION

Accordingly the present invention provides a process for obtaining phenanthrene of about 95% purity from coal tar distilled fraction containing crude phenanthrene by performing fractional distillation at a reduced pressure of 50 mm mercury and at a temperature range of 160-180° C. to obtain first distilled fraction containing acenaphthene and fluorene; a second distillate fraction at a temperature range of 200-230° C. containing phenanthrene, anthracene and traces of carbazole; followed by re-distilling the second distillate fraction at a temperature range of 210-224° C. to finally obtaining the pure phenanthrene and a residue which is again used for the recovery of residual phenanthrene by re-distillation at a temperature range of 210-224° C.

BRIEF DESCRIPTION OF THE ACCOMPANYING DRAWINGS

FIG. 1 represents a flow chart of obtaining pure phenanthrene, wherein
1 Feed Pump
2 Pre-heater
3 Kettle type re-boiler
4 Thermic boiler
5 Distillation column
6 Condenser
7 Hot Catch Pot
8 Receiver
9 Product of $2^{nd}$ Cut receiving means
10 Product of $1^{st}$ Cut receiving means
11 Vacuum Pump
12 Heat generating means
13 Heavy Product receiving means
14 Receiving means for receiving pure phenanthrene

DETAILED DESCRIPTION OF THE INVENTION

Accordingly, the present invention provides a process for obtaining phananthrene of about 95% purity from coal tar distilled fraction containing crude phenanthrene by performing fractional distillation at a reduced pressure of 50 mm mercury and at a temperature range of 160-180° C. to obtain first distilled fraction containing acenaphthene and fluorene; a second distillate fraction at a temperature range of 200-230° C. containing phenanthrene, anthracene and traces of carbazole; followed by re-distilling the second distillate fraction at a temperature range of 210-224° C. to finally obtain the pure phenanthrene and a residue which is again used for the recovery of residual phenanthrene by re-distillation at a temperature range of 210-224° C.

One embodiment of the invention provides a process from which 95% pure phenanthrene is obtained, in addition, other products like acenaphthene, flourene, anthracene and carbazole are being separated from the crude phenanthrene.

One more embodiment of the invention relates to a system for obtaining about 95% pure phenanthrene from coal tar distilled fraction, said system comprising of:
(a) a feed pump (1) through which the fraction containing crude phenanthrene is delivered to pre-heater (2),
(b) sending the material from pre-heater (2) of step (a) to a kettle-type re-boiler (3) and obtaining a super-heated vapor,
(c) sending the super heated vapor of step (b) to distillation column (5) and then to a condenser (6) to obtain a distilled product,
(d) collecting the distilled product of step (c) containing pure phenanthrene into a hot catch pot (7) and the overflow from hot catch pot is sent to a receiver (8) using a vacuum pump (11), (e) discharging a residue containing heavy products from kettle-type boiler (3) into a receiving means (13);

(f) obtaining first cut out distillate and a second cut out distillate fractions in (10) and (9) respectively from the receiver (8) based on temperature variations and if desired, (g) re-distilling the second cut-out distillate fraction (9) of step (f), by sending it to kettle type re-boiler (3) and repeating steps (c) and (d) and then discharging the pure phenanthrene into the receiving means (14).

Another embodiment of the invention relates to a system, which is having continuous circulation of hot-thermic oil from thermic boiler (4) to kettle re-boiler (3) thereby to preheater (2) and finally back to thermic boiler (4) leading to conservation of heat.

Still another embodiment, the heat generated in condenser (6) can be sent to a heat generating means (12) thereby recovering heat.

Still another embodiment, the heat recovery means is a hot water generation means (12), which prevents solidification of product and thereby avoiding choking of the condenser (6).

Yet another embodiment, the product of hot catch pot (7) is sent to distillation column (5) for re-distillation.

Yet another embodiment of the invention provides a system, in which the first cut product from the receiving means (10) can be sent to the kettle type boiler (3) for carrying out re-distillation.

Yet another embodiment, the phenanthrene obtained has a purity of 95% which is recovered from the recovery means (14).

Yet another embodiment of the invention provides separation of acenaphthene, flourene, anthracene and carbazole from crude phenanthrene.

One more embodiment of the invention, the separation is effected by suitably modifying the parameters of temperature and pressure.

Another embodiment of the invention, the percentage yields of various products as follows.

Lighter products—Acenaphthene and fluorene about 15 to 18%

Carbazole and other heavy products about 27 to 33%

Phenanthrene about 50-55%.

Acenaphthene and fluorene, the lighter products are collected at (10)

Product from hot catch pot (7) is refluxed to (5) for developing the purity of phenanthrene. From distillation column (5), heavier fractions remains at bottom whereas the lighter fractions goes as condensate to (6) and (7). This process is continued several times to get purity of product.

Hot catch pot (7) has been partitioned into two and valves control collections at the parts. One part goes to (8) as the main product whereas other part is refluxed to distillation cloumn (5) for re-distillation. The objective of this to obtain pure phenanthrene as much as possible.

The differentiation of fractions at distillation column (5) is done by the observance of temperature at (5). For first distillation, if the temperature is maintained in between 190to 214° C. then it is sent to (10) and if it is in between 214-228° C. it is sent to (9). In case of re-distillation of product at (9), the temperature is maintained in between 215-223° C. Controlling valves performs the above operations.

The heavy products are carbazole, flourenthrene and other tarry products, which are obtained above 400° C. Practically the heavier products are not taken into consideration. From kettle type re-boiler (3), after superheated vapors are transferred to (5) for re-distillation, the residue is collected at (13).

The function of the vacuum pump (11) is to create lower vapor pressure, thereby lowering boiling points of various fractions.

Steam created at (12) is circulated to condenser (6) and the same is re-circulated again and again from 6→ to 12, 12→6 etc,. the purpose of steam is to prevent the condenser from choking as melting point of phenanthrene is 101° C.

The temperature maintained at different points are:
(2) 150 to 200° C.,
(3) 230-250° C.,
(4) 250-300° C.;
(5) 224-230° C.;

Hot oil is circulated between (3), (2), (4) and (3).

The novel features of the invention are:
1. Phenanthrene of 95% purity could be obtained from crude phenanthrene, the literature for which is not available elsewhere.
2. The system, has the provision to use steam generated from the condenser (6) for the distillation of the entire fractions thereby choking of pipelines could be avoided by this construction.

The following examples are given by way of illustration of the present invention and should not be construed to limit the scope of the present invention.

EXAMPLE-1

1100 gms of crude phenanthrene was subjected to distillation. The various product break-ups are indicated without taking into account of other residues. The first cut was distilled in the range of 190 to 214 degree Celsius wherein 130 gms of the product (43.53 gms of Phenanthrene, 9.364 gms of Acenaphthene; 72.605 gms of fluorene) was obtained. The second cut was distilled in the range of 220 to 232 degree Celsius wherein 788 gms of the product (727.311 gms of Phenanthrene, 8.97 gms of Carbazole and 36.48 gms of Acenaphthene) was obtained. From the bottom part, 175 gms of the product (94.46 gms Phenanthrene and 80.54 gms of Carbazole) was obtained. The residue of the second cut was 753 gms and was subjected to re-distillation; the first cut was distilled in the temperature range of 220 to 223 degree Celsius from which 118 gms of the product (23.53 gms of Acenaphthene, 71.97 gms of Phenanthrene and 0.82 gms of Carbazole) was obtained; the second cut was distilled in the temperature range of 224 to 230 degree Celsius from which 531 gms of the product (516 gms of Phenanthrene, 5.99 gms of Acenaphthene and 8.03 gms of Fluorene ) was obtained; distillation of bottom part yielded 103 gms of the product (0.193 gms of Fluorene, 68.04 gms of Phenanthrene and 34.76 gms of carbazole) was obtained.

EXAMPLE-2

1100 gms of crude phenanthrene was subjected to distillation. The various product break-ups are indicated without taking into account of other residues. The first cut was distilled in the range of 160 to 180 degree Celsius wherein 60 gms of the product (16.8 gms of Phenanthrene, 43.2 gms of Acenaphthene) was obtained. The second cut was distilled in the range of 200 to 230 degree Celsius wherein 853 gms of the product (737.477 gms of Phenanthrene, 36.4120 gms of Carbazole and 79.112 gms of Acenaphthene) was obtained. From the bottom part, 185 gms of the product (38.216 gms Phenanthrene and 146.783 gms of Carbazole) was obtained. The residue of the second cut was 793 gms and was subjected to re-distillation; the first cut was distilled in the temperature range of 210 to 224 degree Celsius from which 131 gms of the product (44.89 gms of Acenaphthene, 86.11 gms of Phenanthrene) was obtained; the second cut was distilled in the temperature range of 224 to 230 degree Celsius from which 586 gms of the product (559.45 gms of Phenanthrene, 19.80 gms of Acenaphthene and 6.75 gms of carbazole) was obtained; distillation of bottom part yielded 72 gms of product (57.0 grams of Phenanthrene and 26.42 gms of carbazole) was obtained.

EXAMPLE-3

1000 gms of crude phenanthrene was subjected to distillation. The various product break-ups are indicated without taking into account of other residues. The first cut was distilled in the range of 150 to 165 degree Celsius wherein 14 gms of the product (3.85 gms of Phenanthrene, 10.17 gms of Acenaphthene) was obtained. The second cut was distilled in the range of 180 to 228 degree Celsius wherein 779 gms of the product (673.50 gms of Phenanthrene, 33.25 gms of Carbazole and 72.25 gms of Acenaphthene) was obtained. From the bottom part, 197 gms of the product (40.70 gms Phenanthrene and 156.30 gms of Carbazole) was obtained. The residue of the second cut was 769 gms and was subjected to re-distillation; the first cut was distilled in the temperature range of 167 to 214 degree Celsius from which 140 gms of the product (47.98 gms of Acenaphthene, 92.02 gms of Phenanthrene) was obtained; the second cut was distilled in the temperature range of 214 to 226 degree Celsius from which 472 gms of the product (450.61 gms of Phenanthrene, 15.95 gms of Acenaphthene and 5.431 gms of Fluorene) was obtained; distillation of bottom part yielded 149 gms of the product (54.676 gms of carbazole and 94.324 gms of Phenanthrene) was obtained.

The main advantages of the present invention are:
1. Recycling of different cuts could separate acenaphthene, fluorene and carbazole, which are also useful chemicals.
2. The chemicals and solvents used in the process are very cheap; thereby the process is cost effective.

The invention claimed is:

1. A process for obtaining phenanthrene of about 95% purity from coal tar containing acenaphtene, flourene, anthracene, carbazole, pyrene and phenanthrene, said process comprising the steps of:
   a) fractional distillation of coal tar at a reduced pressure of 50 mm Hg;
   b) heating the coal tar at a temperature of 160° C. to 180° C. to obtain vapors;
   c) condensing the vapors to obtain a first distillate fraction containing acenaphthene and flourene;
   d) obtaining a second distillate fraction at 200° C. to 230° C. containing phenanthrene, anthracene and traces of carbazole;
   e) re-distilling the second distillate fraction at a temperature range of 210 to 224° C. to obtain phenanthrene of about 95% purity and a residue which is again used for the recovery of residual phenanthrene by redistillation at a temperature range of 210° C. to 224° C.

2. A process as claimed in claim 1, wherein the residues in step e) are pyrene and carbazole.

* * * * *